United States Patent [19]

Murata et al.

[11] Patent Number: 5,486,585
[45] Date of Patent: Jan. 23, 1996

[54] AMIDOSILYLDIYL BRIDGED CATALYSTS AND METHOD OF POLYMERIZATION USING SAID CATALYSTS.

[75] Inventors: Masahide Murata, Ohi, Japan; Terry J. Burkhardt, Kingwood, Tex.

[73] Assignee: Exxon Chemical Patents Inc., Wilmington, Del.

[21] Appl. No.: 112,491

[22] Filed: Aug. 26, 1993

[51] Int. Cl.⁶ .................................................. C08F 4/656
[52] U.S. Cl. .................. 526/130; 526/124.9; 526/126; 526/127; 526/129; 526/160; 502/102; 502/117; 502/152; 502/153; 502/155
[58] Field of Search ................................. 502/102, 103, 502/104, 114, 117, 152, 153, 155; 526/126, 127, 160, 170, 125, 129, 130, 160, 904

[56] References Cited

U.S. PATENT DOCUMENTS

| | | | |
|---|---|---|---|
| 4,769,510 | 9/1988 | Kaminsky et al. | 585/512 |
| 4,808,561 | 2/1989 | Welborn, Jr. | 502/104 |
| 4,871,705 | 10/1989 | Hoel | 502/117 |
| 4,931,417 | 6/1990 | Miya et al. | 502/117 |
| 4,985,576 | 1/1991 | Rohrmann et al. | 556/435 |
| 5,017,714 | 5/1991 | Welborn, Jr. | 556/12 |
| 5,026,798 | 6/1991 | Canich | 526/127 |
| 5,055,438 | 10/1991 | Canich | 502/117 |
| 5,145,819 | 9/1992 | Winter et al. | 502/117 |
| 5,198,401 | 3/1993 | Turner et al. | 502/155 |
| 5,225,500 | 7/1993 | Elder et al. | 526/127 |
| 5,240,894 | 8/1993 | Burkhardt et al. | 502/108 |

FOREIGN PATENT DOCUMENTS

| | | |
|---|---|---|
| 0277003 | 8/1988 | European Pat. Off. . |
| 0129368 | 7/1989 | European Pat. Off. . |
| 0413326 | 2/1991 | European Pat. Off. . |
| 0485823 | 5/1992 | European Pat. Off. . |
| 0485820 | 5/1992 | European Pat. Off. . |
| 0485821 | 5/1992 | European Pat. Off. . |
| 0485822 | 5/1992 | European Pat. Off. . |
| 0520732 | 12/1992 | European Pat. Off. . |
| 5-230135 | 9/1993 | Japan ..................... 526/126 |

OTHER PUBLICATIONS

Kaminsky, W., "Metallocene Catalysts", SP '92–Polyethylene World Congress, Zürich, 1992, pp. 1–20.

Jutzi, et al., "Mono–and Bis($\eta^1$–pentamethylcycopentadienyl)silane–Synthese, Stuktur and Eigenschaften," *Chemical Ber*, 121, pp. 1299–1305, Weinheim, 1988.

Sax Irving N. and Richard J. Lewis, Sr. (eds.), "Periodic table of the elements", *Hawley's Condensed Chemical*, p. 6.

*Primary Examiner*—Romulo H. Delmendo
*Attorney, Agent, or Firm*—M. Susan Spiering; C. Paige Schmidt

[57] ABSTRACT

Disclosed is a mono- or di-amido siladiyl bridged composition of matter useful as a catalyst component for the homo or copolymerization of olefins.

19 Claims, 2 Drawing Sheets

AMIDOSILYLDIYL BRIDGED CATALYSTS AND METHOD OF POLYMERIZATION USING SAID CATALYSTS.

FIELD OF THE INVENTION

This invention relates generally to bridged catalyst systems and more particularly to bridged transition metal catalyst components having mono or di-amido siladyl bridging groups. The invention also relates to methods of making and using the catalyst components.

BACKGROUND OF THE INVENTION

Polymers made employing catalyst systems having bridging atom(s) of one or more carbon, silicon, germanium, phosphorous, or nitrogen atom(s) are known (U.S. Pat. No. 4,985,576, EPA 129368). Most typical are ethylene-bridged systems in which two carbon atoms link substituted or unsubstituted cyclopentadienyl or indenyl moieties. (U.S. Pat. No. 4,931,417; EPA 485,820; U.S. Pat. No. 5,017,714).

For example, Hoechst AG, of Germany, discloses carbon bridged indenyl catalyst components which are chiral and useful for the production of high molecular weight isotactic polypropylene ("IPP") (EPA 413,326; EPA 485,822; EPA 485,823; U.S. Pat. No. 4,769,510 and U.S. Pat. No. 5,145,819). EPA 485,821 discloses indenyl catalyst components bridged with carbon-silicon, germanium-silicon, or tin-silicon combination of atoms. These catalyst components are useful in the production of IPP having a melting point of about 150° C. or greater.

Catalyst components having mono or diamido siladyl bridging cyclopentadienyl groups are not well known. Jutzi, et al., disclosed in *Chemical Ber*, 1988, 121, 1299 preparation of a siladiyl-amine-bridge pentamethyl cyclopentadienyl derivative. However, this derivative is not a catalyst component, nor can it be converted to a cyclopentadienyl catalyst component since no transition metal is present.

It would be desirable to provide a novel catalyst component which can be useful for the polymerization of olefins or alpha-olefins wherein the catalyst component comprises mono- or diamido-siladiyl bridging atoms.

SUMMARY OF THE INVENTION

Accordingly, the present invention provides transition metal catalyst component comprising mono-or diamido-siladiyl bridged compositions useful as catalyst components for the polymerization of monomers, especially olefinic monomers. This invention provides a method for preparing such catalyst compositions. The inventive catalyst component is useful for the production of homo- or copolymers having varying molecular weights and melting points. The catalyst components yield polymers of relatively narrow molecular weight distribution. The catalyst component comprises a bridging group having at least one nitrogen bonded to a silicon atom, which silicon atom is bonded to at least one ligand coordinated with a transition metal.

The catalyst composition is represented by the general formula

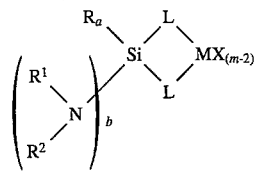

(1)

wherein L is an anionic ligand and can be the same or different
(i) $Cp_z$;
(ii) O; or
(iii) $NR^3$;
wherein:
M is a Group 3–6 transition metal, preferably Group 4;
X is same or different hydrogen, halogen, hydrocarbyl, substituted hydrocarbyl, halocarbyl, substituted halocarbyl, $C_{1-20}$ alkyl, $C_{2-20}$ alkenyl, preferably $C_{2-10}$ alkenyl, $C_{6-20}$ aryl, preferably $C_{6-10}$ aryl, $C_{7-40}$ alkylaryl, preferably $C_{7-20}$ alkylaryl, $C_{7-40}$ arylalkyl, preferably $C_{7-20}$ arylalkyl, $C_{8-40}$ arylalkenyl, preferably $C_{8-20}$ arylalkenyl, alkoxy, aryloxy, siloxy, amide radicals or combinations thereof;
Cp is the same or different cyclopentadienyl ring substituted with from zero to four substitutent groups, each group being, independently, the same or different hydrocarbyl, substituted hydrocarbyl, silahydrocarbyl, halocarbyl, substituted halocarbyl, or taken together, two or more adjacent carbons form part of a ring structure having between 2 and 10 carbons.
m is equal to or greater than 2 and is the oxidation state of the transition metal;
z=0, 1, or 2
R, $R^1$, $R^2$, $R^3$ are the same or different hydrogen, halogen, $C_{1-20}$ alkyl, $C_{2-20}$ alkenyl, preferably $C_{2-10}$ alkenyl, $C_{6-20}$ aryl, preferably $C_{6-10}$ aryl, $C_{7-40}$ alkylaryl, preferably $C_{7-20}$ alkylaryl, $C_{7-40}$ arylalkyl, preferably $C_{7-20}$ arylalkyl, $C_{8-40}$ arylalkenyl, preferably $C_{8-20}$ arylalkenyl, or taken together, two or more adjacent carbons form part of a ring structure having between 2 and 10 carbons, alkoxy, ketones, SiR, SiOR, NR, SR, AlR, PR;
Si is silicon;
N is nitrogen;
a=b=1, or a=0 and b=2;
when b=2, the formula may alternatively be represented by

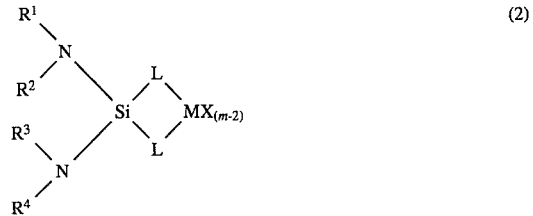

(2)

wherein $R^4$ is as defined for R, $R^1$, $R^2$, $R^3$.

An alternative embodiment of the composition is represented by general formula

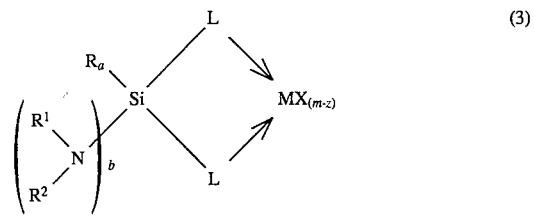

(3)

wherein L is a neutral ligand and can be the same or different
(i) $Cp_z$; or
(ii) $OR^3$; or,
(iii) $NR^4R^5$;
wherein $R^4R^5$ are as defined for R, $R^1$, $R^2$ above;
Cp, X, R, $R^1$, $R^2$, $R^3$, Si, N, M, z, m, a, and b are as defined for formula (1).

Formula (3) may also be represented with the bridging structure of formula (2) for the diamido version of the siladyl bridge derivative.

The prefered catalyst composition is represented by formula (4)

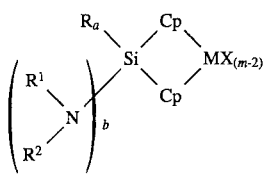

wherein all symbols are as defined above. Formula (4) may also be represented with the bridging structure of formula (2) for the diamido version of the siladiyl bridge derivative.

The catalyst composition is converted to a catalyst system by reaction with a catalyst activating compound, such as alumoxane, or methylalumoxane. Alternatively, the catalyst composition is converted to a catalyst system by combining with a single or mixed compound that will form a charge balanced catalytic species. Examples of these compounds are tris(pentafluorophenyl)borane, or an ionic complex comprising a non-coordinating anion.

The catalyst composition or catalyst system may be placed on a support, and optionally prepolymerized before use.

The catalyst system, supported or in homogeneous form, may be used in the polymerization of monomers such as alpha olefins, olefins, diolefins, cyclic olefins or acetylenically unsaturated monomer(s) for the production of polymers. Polymerization may occur via known techniques such as gas phase, bulk, solution, slurry or high pressure polymerization.

DESCRIPTION OF PREFERRED EMBODIMENT

The present invention provides novel mono- or diamidosilyldiyl bridged catalyst components represented by general formulae (1) (2) (3) and (4) above.

Any reference to Group or Groups shall refer to Groups as listed in the Periodic Table of Elements as described in the New IUPAC notation in Hawley's Condensed Chemical Dictionary, Eleventh Edition, revised by Sax and Lewis, Van Nostrand Reinhold, New York, 1987.

A. CATALYST COMPONENT

The catalyst component may contain ligands which are asymmetrically or symmetrically associated with the metal center. Prefered substituted or unsubstituted ligands, L, on the catalyst component include the same or different cyclopentadienyl, indenyl, tetrahydroindenyl, fluorenyl, oxygen, nitrogen, phosphorous, and the like, or derivatives thereof.

Prefered silicon bridging group substituents, R, $R^1$, $R^2$, $R^3$, $R^4$ which are exemplified include: H, halogen, $C_{1-20}$ alkyl, $(CH_3)_2N$,

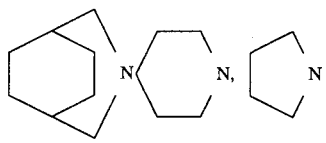

Prefered catalyst components found to be useful for the production of stereoregular alpha-olefin polymers include

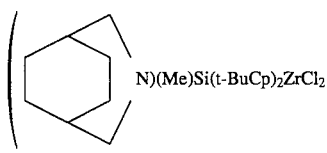

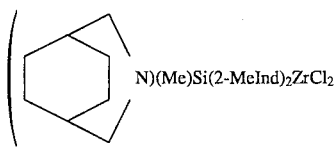

$(Me_2N)_2Si(t-BuCp)_2ZrCl_2$ $(Me_2N)_2Si-(2-MeInd)_2ZrCl_2$

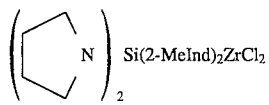

$[(CH_3)_2N]_2Si(3-MeCp)_2ZrCl_2$ $(dicyclohexylamine)_2Si(2-MeInd)_2ZrCl_2$ wherein Me=methyl, Ind=indenyl, Bu=butyl.

B. METHOD TO MAKE CATALYST COMPONENT

At all times, the individual ingredients as well as the recovered components are protected from oxygen and moisture. Therefore, the reactions must be performed in an atmosphere free of these contaminants. Preferably the reactions are performed in the presence of an inert dry gas, such as nitrogen or argon. The recovered catalyst component is maintained in an inert atmosphere, such as nitrogen or argon.

Figure 1:
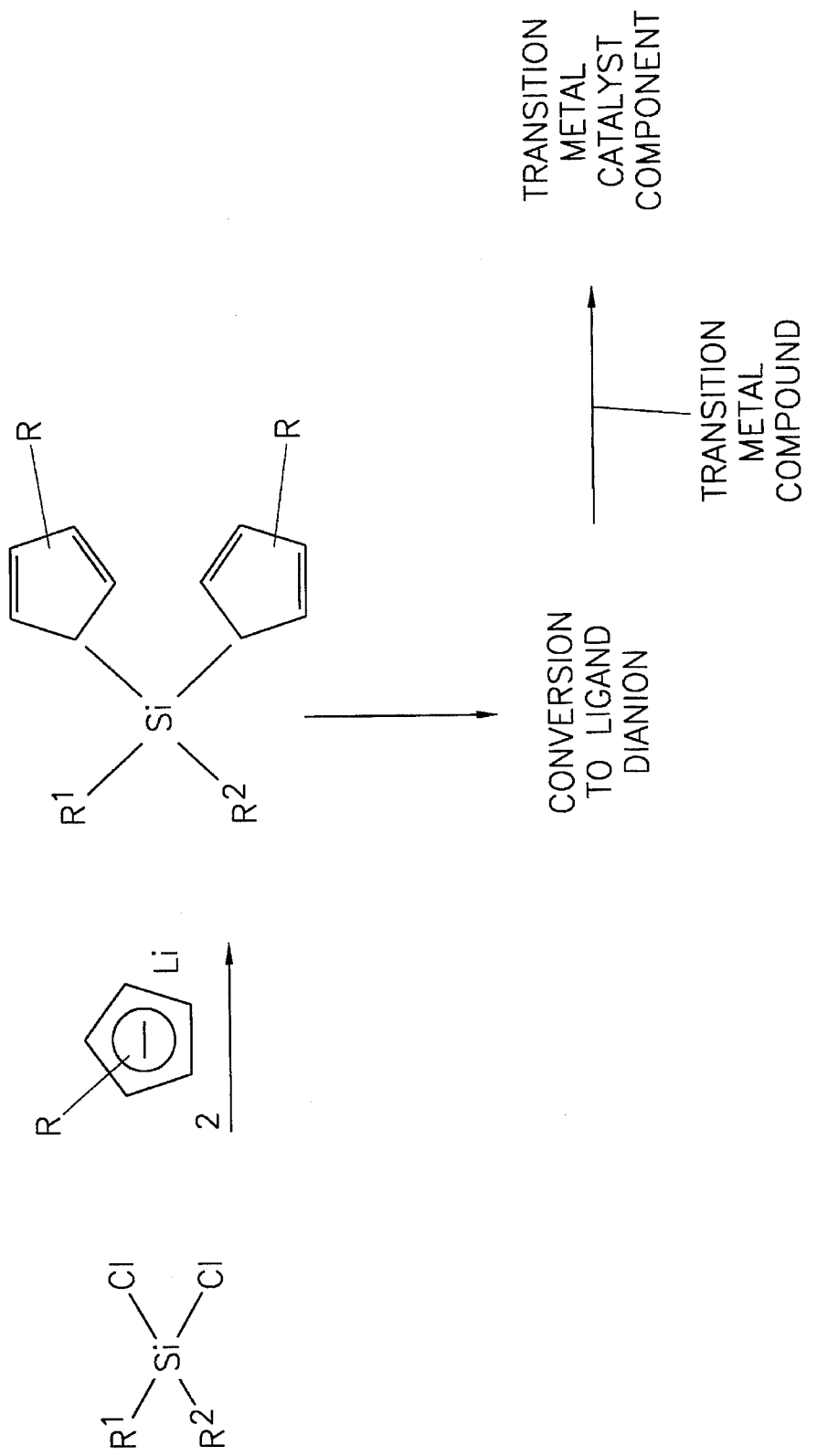

FIG. 1 illustrates a typical synthesis for the production of transition metal components. The route generally involves reaction of a substituted dihalosilyldiyl radical with a lithiated cyclopentadienyl moeity. The reaction product therefrom is reacted with an additional lithiated alkyl compound and finally with a transition metal halide to form the transition metal catalyst component of interest.

The silicon bridged catalyst compositions of the present invention are generally prepared by first building the ligand structure through alkylation/silanylation steps, and then inserting the transition metal using a metal tetrahalide. Lithium and sodium alkyls are preferably used for alkylation steps, however other Group 1 or 2 metals may be employed.

Figure 2:
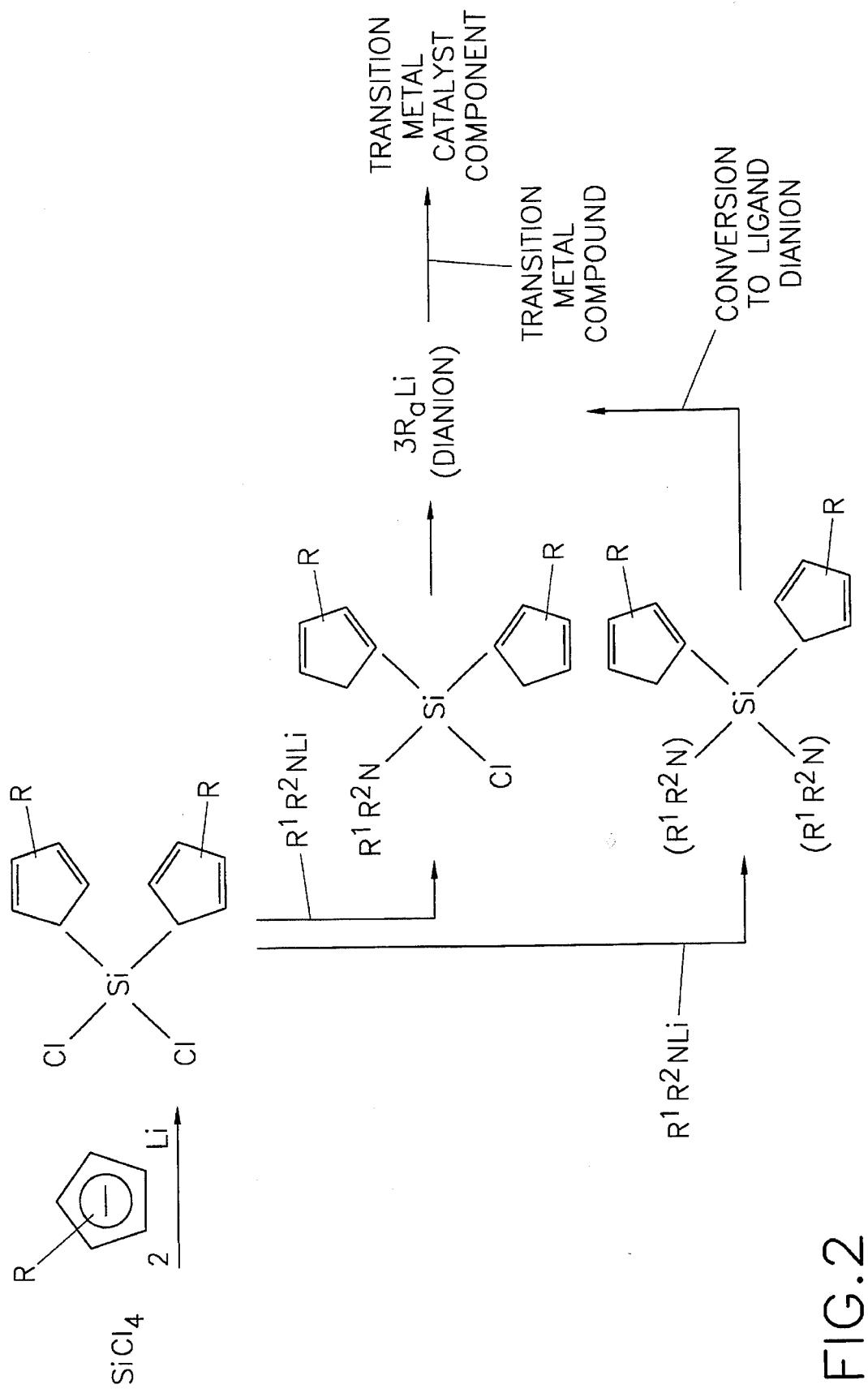

FIG. 2 illustrates the route employed for the production of the inventive catalyst component and illustrates a synthesis where the Cp groups are the same. Alternatively, the reaction of $SiCl_4$ can be carried out in two steps using different lithiated Cp moieties if the desire is to form a catalyst with different Cp rings. If it is desired to form mono Cp or no Cp transition metal structures, the reader is refered to U.S. Pat. No. 5,055,438, herein incorporated by reference.

A method to make the inventive catalyst components described herein comprises the steps of reacting a silicon compound with an amine salt and a charged ligand, $L^-$. More specifically, a method comprises:

a) forming a reaction product of at least one mole of a lithitated salt of ligand L (or a lithiated Cp radical) with a silicon tetrahalide; and b) reacting the product of (a) with at least one mole of a lithium salt of an amine and optionally further reacting with additional amine salt to form the neutral ligand.

To form the desired transition metal component, the product of step (b) is reacted with at least 2 moles of an alkyl metal to form a dianion which is then further reacted with a transition metal.

Although the catalyst component may be employed without purification, purification enhances catalytic performance. For example, in chiral catalyst components, the racemic form may be generally separated from the meso form by crystallization from a solvent such as methylene dichloride using a hydrocarbon diluent, e.g. pentane, as an antisolvent, and recovering the crystallized racemic transition metal component by filtration from the solution in which the meso form generally remains soluble.

C. CATALYST SYSTEM

The bridged and chiral catalyst components described generally have utility in stereoregular polymerization of alpha olefins. Moreover, these catalyst components are broadly useful in the polymerization of monomers such as olefins, including cyclic olefins. They may be used alone, but preferably are reacted with an activating cocatalyst or compound.

The activating compound may include alumoxane, methylalumoxane, a boron containing activator such as tris(pentafluorophenyl)borane, or a compound comprising a non-coordinating anion such as tetra(pentafluorophenyl)boron. For use of boron containing compounds as catalyst activators, see EPA 277003, EPA 520732, and U.S. Pat. No. 5,198,401, all references herein incorporated by reference in their entirety.

The activating compound may be used in ratios of transition metal to activator or activating complex known in the art. For example, if alumoxane is employed as an activator, a molar ratio of Al to metal in the range of about 100,0000:0.5 to about 10:1, preferably between 1000:1 to about 20:1 can be employed. If an activating system which results in a catalyst system comprising a non coordinating anion is employed, a molar ratio of activator to metal of about 10:1 to about 1:1, preferably about 3:1 to about 1:1 can be employed.

The catalyst system which comprises the siladiyl amine composition with an activator component may optionally be placed on a support (or carrier), according to known techniques, such as those described in U.S. Pat. No. 4,808,561 (Welborn), U.S. Pat. No. 4,871,705 (Hoel) or U.S. Pat. No. 5,240,894 (Burkhardt), all references herein incorporated by reference in their entirety. Supports include organic or inorganic solids. Exemplary supports include silica, alumina, silica-alumina and the like, or combinations thereof. Alternatively, the support may be a magnesium compound, such as $MgCl_2$. Any support material is acceptable provided it does not adversely interfere with the catalyst component or catalyst system.

The catalyst may optionally be prepolymerized by techniques known in the art with olefinic monomer containing between 2 to about 20 carbon atoms.

D. USE OF CATALYST SYSTEM

The catalyst system in accordance with this invention may be used to produce homo- or copolymers of polyolefins such as polyethylene, polypropylene, blends of ethylene/propylene or ethylene and higher alpha olefins (e.g., $C_4$–$C_{20}$) or stereoregular polymers such as isotactic polypropylene. Monomers containing between about 2 to about 20 carbon atoms under suitable polymerization conditions may be employed. The monomers may be alpha olefins, olefins, diolefins, cyclic olefins or acetylenically unsaturated monomer(s). Preferred olefins include ethylene, propylene, 1-butene, isobutylene, 4-methyl-1-pentene, 1-hexene, 1-octene and mixtures thereof. Vinylidene monomers may also be employed, examples which include styrene, cyclohexene, cyclooctene, norbornene or ring alkyl or ring aryl derivatives. Generally the polymerization is carried out in bulk, gas, slurry, solution and high pressure phase reactors. Generally, the polymerization process is carried out with a pressure of from about 70 to about 7000 kPa (about 10 to about 1000 psi), most preferably from about 275 to about 4100 kPa (about 40 to about 600 psi). The polymerization diluent is maintained at a temperature of from about −10° C. to about 150° C., preferably from about 20° C. to about 100° C., and most preferably from about 30° C. to about 90° C. The catalyst system may also be employed in a high temperature/high pressure polymerization process where the presure can range from about 35 MPa to about 275 MPa (about 5,000–40,000 psi) and the temperature can range from about 120° to about 300° C. The polymerization may be carried out as a batch or continuation process.

If desired, an additive may be employed during the polymerization to enhance catalytic performance by neutralizing impurities capable of deactivating the catalyst. Exemplary additives, which generally serve as scavengers in the polymerization process, include aluminum alkyls such as triethylaluminum or triisobutylaluminum. Methylalumoxane may also serve as an additive in the polymerization process.

The amount of additive to employ may be easily determined by monitoring the level of monomer consumption while adding the additive compound to the polymerization diluent. Additive is added to the reactor in an amount sufficient to optimize the rate at which the monitored monomer is consumed in the polymerization reaction.

One or more activator component(s) may be employed during polymerization. Activators are prepared and employed in accordance with techniques known in the art.

EXAMPLES

The preparation of the amido siladiyl bridged catalyst composition of the present invention and use thereof are illustrated by way of the examples that follow.

All experiments were carried out in nitrogen purged dry boxes. Solvents were purchased from commercial sources, nitrogen purged and dried over activated molecular sieves. $ZrCl_4$ was purchased from commercial sources and used as received. MAO was purchased as 10 or 30 wt % (in toluene). All transition metal components were characterized by proton and/or carbon NMR.

The catalyst components of Examples 1–7 were reacted with MAO to form an active catalyst. Polymerization results employing these catalysts are in Table 2. The polymerization procedure, which employed a bulk phase reactor, at a pressure of about 30 kg/cm$^2$ is as follows. In a clean, dry two liter stainless steel autoclave which had been flushed with propylene vapor, MAO (1.0 ml, 10% in toluene) was added and then the reactor closed and filled with 750 ml liquid propylene. The reactor was heated to the desired temperature, generally about 40° C., and the catalyst, prepared by reacting the transition metal component (10 mg in 1.0 ml toluene) with MAO (1.25 ml, 10% MAO in toluene), was washed in via an addition tube with 250 ml propylene. After the desired reaction time, usually about 30 minutes, the reactor was cooled and the excess propylene vented. The polymer was removed and dried.

Polymer analysis was carried out as described in U.S. Pat. No. 5,026,798 and U.S. Pat. No. 5,017,714. Tacticity measurements were determined by 13C NMR as described in "Polymer Sequence Distributions", J. C. Randall, Academic Press, New York, (1986). DSC melting points were determined on commercial DSC instruments and are reported as the second melting point.

EXAMPLE 1

$(C_8H_{14}N)(CH_3)Si(3\text{-}t\text{-}butylC_5H_3)_2ZrCl_2$

Part 1. t-BuCpLi

MeLi (0.183 mol in ether) was added dropwise over 30 min to 6,6-dimethylfulvene (19.466 g, 0.183 mol) dissolved in ether (500 ml, dried over Na and freshly distilled) and cooled to 0° C. After stirring at room temperature for 3 days, the solvent was removed under vacuum. The residual solid was washed twice with n-pentane (200 ml) and dried under vacuum. (t-butylC$_5$H$_4$)Li (20 g, 90%) was obtained as a white powder.

Part 2. $Cl_2Si(3\text{-}t\text{-}BuCp)_2$

To SiCl$_4$ (1.989 g, 0.0117 mol) dissolved in THF (200 ml), t-BuCpLi (3 g, 0.0234 mol) slurried in THF (50 ml) was added dropwise. After stirring at room temperature for 1.5 hrs, the solvent was removed under vacuum, and the residue extracted with n-pentane (200 ml). Cl$_2$Si(3-t-BuCp)$_2$ (4.0 g, 100%) was obtained as a yellowish liquid after evaporation of the n-pentane.

Part 3. $(C_8H_{14}N)Li$

To azabicyclo[3,2,2]nonane (5.0 g) dissolved in ether (200 ml), a solution of MeLi (0.04 mol) was added dropwise with stirring at room temperature. After stirring overnight, the solvent was removed under vacuum. The residual solid was washed twice with n-pentane (200 ml) and dried under vacuum. C$_8$H$_{14}$NLi (3.8 g, 73%) was obtained as a white powder.

Part 4. $(C_8H_{14}N)(Cl)Si(3\text{-}t\text{-}BuCp)_2$

To Cl$_2$Si(t-BuCp)$_2$ (2 g) dissolved in ether (200 ml) C$_8$H$_{14}$NLi (0.769 g) dissolved ether (100 ml) was added dropwise. After stirring overnight at room temperature the solvent was removed under vacuum, and the residue extracted with n-pentane (200 ml). (C$_8$H$_{14}$N)(Cl)Si(3-t-BuCp)$_2$ (2.35 g, 93%) was obtained as a yellow, clear oil.

Part 5. $(C_8H_{14}N)(Me)Si(3\text{-}t\text{-}BuCp)_2ZrCl_2$

To (C$_8$H$_{14}$N)(Cl)Si(3-t-BuCp)$_2$ (2.35 g, 5.46×10$^{-3}$ mol) dissolved in ether (200 ml) an ether solution of MeLi (0.0164 mol) was added dropwise. After stirring overnight at room temperature, the solution was cooled to 0° C. and ZrCl$_4$ (1.273 g) was added. After stirring overnight, evaporation of ether, extraction with n-pentane, and recrystallization at −20° C., (C$_8$H$_{14}$N)(Me)Si(3-t-BuCp)$_2$ZrCl$_2$, was obtained (0.1 g).

EXAMPLE 2

$(C_8H_{14}N)(Me)Si(C_9H_6)_2ZrCl_2$

Part 1. Indenyl Lithium ("INDLi")

To Indene (14.52 g) dissolved in ether (250 ml), n-Butyl Lithium (50 ml, 2.5 mol/l in hexane solution) was added dropwise. By repeating the purification procedure of t-BuCpLi in Example 1, Part 1, indenyl lithium (13.5 g, INDLi) was recovered.

Part 2, $Cl_2Si(C_9H_7)_2$

To SiCl$_4$ (5.56 g) dissolved in ether (200 ml), INDLi (8 g) in ether was added dropwise and stirred overnight. By repeating the purification procedure in Example 1, Part 2, Cl$_2$Si(C$_9$H$_7$)$_2$ (10.3 g, 96%) was obtained as a yellowish oily solid.

Part 3, $(C_8H_{14}N)(Cl)Si(C_9H_7)_2$

To Cl$_2$Si(C$_9$H$_7$)$_2$ (5.9 g) dissolved in ether (200 ml) an ether solution of C$_8$H$_{14}$NLi (2.35 g) was added. After stirring overnight at room temperature, the same purification procedure in Example 1 Part 4, was used. (C$_8$H$_{14}$N)(Cl)Si(C$_9$H$_7$)$_2$ (7 g, 93%) was obtained as a yellowish white waxy solid.

Part 4, $(C_8H_{14}N)(Me)Si(C_9H_6Li)_2$

To (C$_8$H$_{14}$N)(Cl)Si(C$_9$H$_7$)$_2$ (3 g) dissolved in ether (200 ml), MeLi (0.0216 mol ) was added dropwise and stirred overnight. The purification procedure for t-BuCpLi in Example 1, Part 1, was used to give (C$_8$H$_{14}$N)(Me)Si(C$_9$H$_6$Li)$_2$ (3.17 g,100%) as a pale pink powder.

Part 5, $(C_8H_{14}N)(Me)Si(C_9H_6)_2ZrCl_2$

To (C$_8$H$_{14}$N)(Me)Si(C$_9$H$_6$Li)$_2$ (3.17 g) dissolved in ether (200 ml) and cooled to 0° C., ZrCl$_4$ (1.807 g) was added and stirred at room temperature overnight. After evaporation of the ether, the residual solid was extracted with CH$_2$Cl$_2$ (200 ml). Evaporation and twice washing with n-pentane (100 ml) gave (C$_8$H$_{14}$N)(Me)Si(C$_9$H$_6$)$_2$ZrCl$_2$ (2.4 g, 56%) as an orange/brown solid.

EXAMPLE 3

$[(CH_3)_2N]_2Si(3\text{-methylcyclopentadienyl})_2ZrCl_2$

Part 1: (MeCpLi)

To freshly distilled methyl cyclopentadiene monomer (30 g) dissolved in ether (600 ml), n-buthyl lithium (150 ml, 2.5M in hexanes) was added dropwise over one hour. After stirring 3 days, the solids were collected by filtration, washed twice with pentane (200 ml), and dried to give MeCpLi (29.5 g, 92%) as a white powder.

Part 2: $(Cl_2Si(MeCp)_2)$

To a solution of SiCl$_4$ (2.965 g) in THF (200 ml) MeCpLi (3 g) in THF was added dropwise over 30 minutes. After stirring for 90 minutes, the THF was evaporated under vacuum. The residue was extracted with n-pentane (200 ml). From the n-pentane solution Cl$_2$Si(3-MeCp)$_2$ (4.06 g, 90%) was recovered.

Part 3: $(Me_2N)_2Si(3\text{-}MeCp)_2$

To Cl$_2$Si(MeCp)$_2$ (2 g) dissolved in ether (200 ml), Me$_2$NLi (0.794 g suspended in 50 ml of ether) was slowly added. After stirring overnight, the same purification procedure in Example 1, Part 2, was used to give (Me$_2$N)$_2$Si(3-MeCp)$_2$ (2.0 g,94%) as a yellow, oily liquid.

Part 4: $(Me_2N)_2Si(3\text{-}MeCpLi)_2$

To (Me$_2$N)$_2$Si(3-MeCp)$_2$ (2.0 g) dissolved in ether (200 ml), MeLi (0.0146 mol) in ether was added dropwise. After stirring overnight, the solvent was evaporated. The residual solid was washed twice with n-pentane (100 ml) and dried under vacuum to give ((Me$_2$N)$_2$Si(3-MeCpLi)$_2$ (2.1 g) as a white powder.

Part 5: $(Me_2N)_2Si(3\text{-}MeCp)_2ZrCl_2$

To (Me$_2$N)$_2$Si(3-MeCpLi)$_2$ (2.1 g) dissolved in ether (200 ml) and cooled to 0° C., ZrCl$_4$ (1.705 g) was added, and the reaction mixture stirred for 3 days at ambient temperature. After evaporation of the solvent, the residue was extracted with pentane to give (Me$_2$N)$_2$Si(MeCp)$_2$ZrCl$_2$ (0.96 g).

EXAMPLE 4

$(C_8H_{14}N)(methyl)Si(2\text{-methylindenyl})_2ZrCl_2$

Part 1: 2-methylindene

To an ether solution of MeMgBr (260 ml, 3M) diluted with ether (300 ml) and cooled to 0°C, 2-methylindanone (99.16 g) was added dropwise as an ether solution over 2.5 hours. After stirring 2.0 hours, the reaction mixture was hydrolyzed with aqueous HCl. The water phase was separated and extracted twice with ether (300 ml). The combined organic phases were dried over sodium sulfate. Evaporation of the solvent gave a crude brown product (107 g) which was distilled under reduced pressure to give 2-methyl-2-indanol (66.2 g) as a white crystalline solid.

2-Methyl-2-indanol (66.2 g) was dissolved in toluene (500 ml) in a 1 liter flask equipped with a Dean-Stark trap. To this solution p-toluene sulfonic acid (2 g) and a small amount of hydroquinone were added, and the mixture was refluxed for 2.5 hours. After 8 ml of $H_2O$ was generated, the reaction mixture was cooled to 0° C. and $H_2O$ (1 liter), also cooled to $0^3C$, was added. The organic phase was separated and washed three times with water (500 ml). The toluene was evaporated and the residue (with trace of hydroquinone added) was distilled at reduced pressure to give 2-methyl-indene (47.2 g, 48%) as clear slightly green liquid.

Part 2: 2-methylindenyl lithium 2-methylindene (47.2 g) was dissolved in ether (400 ml) and n-butyl lithium (145.2 ml, 2.5M in Hexane) was added dropwise over 3 hours. The mixture was stirred for 2.5 hours. After evaporation of the solvent, the residual solid was washed twice with n-pentane (400 ml). Drying under vacuum gave 2-methylindenyl lithium (42 g, 85%) as a pale brown powder.

Part 3: $Cl_2Si(2\text{-Me-IND})_2$

The procedure of Example 1, Part 2, was followed except using $SiCl_4$ (2.5 g) and 2-MeINDLi (4 g). $Cl_2Si(2\text{-MeIND})_2$ (4.79 g, 91%)) was obtained as a yellowish, slightly waxy solid.

Part 4: $(C_8H_{14}N)$ $(Me)Si(2\text{-Me-INDLi})_2$

The preparation procedures Example 2, Part 3, and Part 4 was repeated except using $Cl_2Si(2\text{-Me-IND})_2$ (4.79 g) in place of $Cl_2Si(IND)_2$. $(C_8H_{14}N)(Me)Si(2\text{-Me-INDLi})_2$ (5.55 g) was recovered as a pale yellow powder.

Part 5: $(C_8H_{14}N)(Me)Si(2\text{-Me-IND})_2 ZrCl_2$ $ZrCl_4$ (2,635 g) was suspended in $CH_2Cl_2$ (300 ml) and cooled to −78° C. To this suspension, $(C_8H_{14}N)(Me)Si(2\text{-MeIND})_2$ (5.55 g) was added and stirred at −78° C. for 8 hours. After raising to −30° C., the mixture was allowed to warm to room temperature overnight. The mixture was dried, and the residue extracted with $CH_2Cl_2$ for six days to give $[(C_8H_{14}N)(Me)Si(2\text{-Me-IND})_2 ZrCl_2]$ as an orange powder (3.7 g).

EXAMPLE 5

$(CH_3)_2N]_2Si(2\text{-methyl-Indenyl})_2 ZrCl_2$ synthesis

Part 1: $(Cl_2Si(2\text{-Me-IND})_2$

The procedure in Example 4, Part 3, was repeated except using $SiCl_4$ (5 g) and 2-MeINDLi (8 g) to gave $Cl_2Si(2\text{-methylIND})_2$ (9.36 g, 89%).

Part 2: $(Me_2N)_2 Si(2\text{-Me-IND})_2$

Following the procedure in Example 3, Part 3, except using $Cl_2Si(2\text{-Me-IND})_2$ (4.73 g) and $Me_2NLi$ (1.42 g), gave $(Me_2N)_2Si(2\text{-MeIND})_2$ (4 g) as a yellow oil.

Part 3: $Me_2N)_2 Si(2\text{-Me-INDLi})_2$

Following the procedure of Example 3, Part 4, except using $(Me_2N)_2Si(2\text{-MeIND})_2$ (4 g), and MeLi (0.0216 mol) gave $(Me_2N)_2 Si(2\text{-Me-INDLi})_2$ (4 g, 97%) as a white powder.

Part 4: $(Me_2N)_2Si(2\text{-Me-IND})_2ZrCl_2$

Following the procedure of Example 4, Part 5 was repeated except using $(Me_2N)Si(2\text{-Me-INDLi})$ (4 g) and $ZrCl_4$ (2.425 g). The $CH_2Cl_2$ solution was filtered and evaporated. The residue was washed with n-pentane (100 ml) and dried to gave a yellow powder (4.6 g, 83%).

The polymer (9.17 g) obtained from polymerization run of Example 5 and 300 ml of n-heptane were introduced to a 500 ml round bottom flask connected with a reflux condenser. After 2 hours of reflux, the solution was decanted while hot. 300 ml of fresh n-heptane was introduced to the residual polymer and the 2 hour reflux repeated. After filtration and drying, 2.7 g of n-heptane insoluble polymer was recovered. From the n-heptane solution, a total of 6.2 g of gummy polymer was recovered (Tm=147.5° C., Mw=480,000, Mw/Mn=2.6).

The polymer obtained from Example 5 was fractionated using decalin. The decalin insoluble fraction was 35 wt %. $^{13}$C-NMR measurements were carried out for the whole polymer (before decalin fractionation), decalin insoluble fraction and decalin soluble fraction. The results are shown in Table 1 which indicate the insoluble polymer is highly isotactic.

EXAMPLE 6

$(C_4H_8N)_2Si(2\text{-methyl-indenyl})_2ZrCl_2$

Part 1: $(C_4H_8NLi)$

The procedure of Example 1, Part 3, was repeated except using pyrrolidine (5 g) to give $C_4H_8NLi$ (5.1 g) as a white powder.

Part 2: $(C_4H_8N)_2Si(2\text{-ME-IND})_2$

The procedure of Example 5, Part 2, was repeated except with $Cl_2Si(2\text{-Me-IND})_2$ (4.6 g) and $C_8H_{14}NLi$ (1.99 g) to give $(C_4H_8N)_2Si(2\text{-MeIND})_2$ (5.72 g) as an oil.

Part 3: $(C_4H_8N)_2 Si(2\text{-Me-INDLi})_2$

The procedure of Example 3, Part 4, as repeated except with $(C_4H_8N)_2Si(2\text{-Me-IND})_2$ (5.72 g) and MeLi (0.0258 mol) to give $(C_4H_8N)_2Si(2\text{-Me-INDLi})_2$ (5.42 g, 96%) as pale yellow powder.

Part 4: $(C_4H_8N)_2Si(2\text{-Me-IND})_2 ZrCl_2$

The procedure in Example 5, Part 4, was repeated except using $ZrCl_4$ (2.9 g) to give $(C_4H_8N)_2Si(2\text{-Me-IND})_2ZrCl_2$ as a yellow-orange powder (5.6 g).

1 gram of $(C_4H_8N)_2Si(2\text{-Me-IND})_2ZrCl_2$ having 68% rac content was dissolved in 30 mls of methylene chloride solvent. 10 mls of n-pentane was added to the solution and stirred for 15 minutes. The solvent was stripped off via vacuum until crystals begun to appear at which point the mixture was placed in freezer and chilled at −30° C. for about 1 hr. The crystals were isolated in a frit, washed with cold pentane and collected. The procedure was repeated utilizing the collected filtrate until no further crystals appeared (0.7 g, 92% rac content).

Preparation of Ethylene Propylene (EP) Polymer Using Catalyst Component of Example 6:

A. Catalyst Preparation: The catalyst component of Example 6 (4.8 mg., 8.19×10$^{-3}$ mmoles) was pre-activated just prior to the polymerization run with 2.0 mls of a 1M MAO/toluene solution. An additional 10.2 mls of the MAO solution was prepared separately.

B. Polymerization Procedure: Toluene, 400 ml., distilled from benzophenone/sodium then passed through an alumina column while under a nitrogen atmosphere, was added to a 1-liter zipperclave reactor at room temperature. The reactor was then cooled to 0° C., using an IPA bath chiller. A 1M MAO solution (10.2 ml.) was then cannulated into the reactor and allowed to stir for approximately 30 seconds. The pre-activated catalyst solution then followed in the same manner.

While stirring this solution a 60/40 EP monomer mixture (11.08 g.) was allowed to flow into the reactor at a rate of approximately 6.8 kPa/sec (about 1 psi/second). The EP mixture was premixed in a 1 liter stainless steel vessel. Samples were taken at various intervals via a sampling tube connected to the reactor vessel. The reaction was allowed to proceed for 45 minutes at which a conversion of 38.3% was yielded. There was no exotherm during the polymerization. The recovered EP polymer was precipitated in acetone and was completely amorphous.

EXAMPLE 7

(dicyclohexylamino)$_2$Si(2-methylindenyl)$_2$ZrCl$_2$

Part 1: Cl$_2$Si(2-Me-IND)$_2$

The procedure in Example 5, Part 1 was repeated to give Cl$_2$Si(2-Me-IND)$_2$ (10.3 g, 98%).

Part 2: (c-C$_6$H$_{11}$)$_2$N](Cl)Si(2-Me-IND)$_2$

The procedure of (C$_4$H$_8$N)$_2$Si(2-ME-IND)$_2$ in Example 6 was repeated employing 5.14 g of Cl$_2$Si(2-Me-Ind)$_2$ and 2.70 g of (C$_6$H$_{11}$)$_2$NLi. A brown product was obtained. (7.92 g, 110%).

Part 3:

The above procedure was repeated using (C$_6$H$_{11}$)$_2$NLi (1.348 g) to give [c-C$_6$H$_{11}$)$_2$N](Cl)Si(2-MeIND)$_2$ and CH$_2$Cl$_2$ as extraction solvent to give brown oil (4.66 g). (Yield=100%)

Part 4: [(C$_6$H$_{11}$)$_2$N]$_2$Si(2-Me-IND)$_2$)Li$_2$

The procedure Example 6,. Part 4, was repeated except using (C$_6$H$_{11}$N)$_2$ Si(2-MeIND)$_2$ (4.66 g) and MeLi (0.0145 mol) to give a light brown powder (2.6 g, 55%)

Part 5: [(C$_6$H$_{11}$)$_2$N]$_2$Si(2-Me-IND)$_2$ZrCl$_2$

The procedure in Example 5, Part 4, was repeated except using [(C$_6$H$_{11}$)$_2$N]$_2$Si(2-Me-IND)$_2$ Li (2.6 g) and ZrCl$_4$ (1.7 g) to give [(C$_6$H$_{11}$)$_2$N]$_2$Si(2-MeIND)$_2$ZrCl$_2$ as a brown powder (2.6 g).

TABLE 1

Tacticity Measurements for decaline fractionated Polymer of Example 5

| Label Col. | Whole Polymer | Insoluble (IPP region) | Soluble (atactic region) |
|---|---|---|---|
| [mm] | 0.498 | 0.947 | 0.243 |
| [mr] | 0.364 | 0.034 | 0.496 |
| [rr] | 0.138 | 0.019 | 0.260 |

TABLE 2

Results of Polymerzation Runs with Catalyt Component of Ex. 1–7

| | DSC MP (°C.) | Mw (× 10$^{-3}$) |
|---|---|---|
| EXAMPLE 1 | 142.5 | 48 |
| EXAMPLE 2 | 138.3 | 50 |
| EXAMPLE 3 | — | 6 |
| EXAMPLE 4 | 149.2 | 300 |
| EXAMPLE 5 | 152.6 | 500 |
| EXAMPLE 6 | 149.5 | 600 |
| EXAMPLE 7 | 147.5 | 300 |

Conditions: 1.0 liter liq. C$_3$=, 40° C., 1.0 ml 10% MAO as scavenger, 10 mg transition metal catalyst component mixed with 1.25 ml 10% MAO

We claim:

1. A polymerization catalyst system comprising a transition metal catalyst component represented by the formulae:

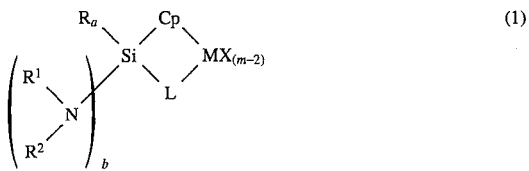

or

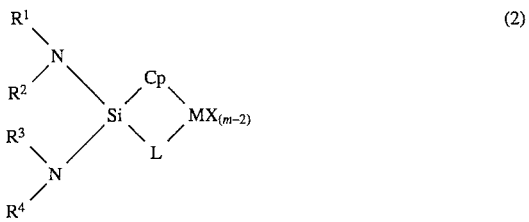

wherein L is an anionic ligand and can be (i) Cp;

(ii) O; or (iii) NR$^3$;

wherein:

M is a group 3–6 transition metal;

X is the same or different hydrogen, halogen, hydrocarbyl, substituted hydrocarbyl, halocarbyl, substituted halocarbyl, C$_{1-20}$ alkyl, C$_{2-20}$ alkenyl, C$_{6-20}$ aryl, C$_{7-40}$ alkyaryl, C$_{7-40}$ arylalkyl, C$_{8-40}$ arylalkenyl, alkoxy, aryloxy, siloxy, or amide radicals or combinations thereof;

Cp is the same or different cyclopentadienyl ring substituted with from zero to four substituent groups, each group being, independently, the same or different hydrocarbyl, substituted hydrocarbyl, hydrocarbyl substituted silyl group, halocarbyl, substituted halocarbyl, or taken together, two or more adjacent substituents form part of a ring structure having between 2 and 10 carbons;

m is equal to or greater than 2 and is equal to the oxidation state of the transition metal;

R, R$^1$, R$^2$, R$^3$, R$^4$ are the same or different hydrogen, halogen, C$_{1-20}$ alkyl, C$_{2-20}$ alkenyl, C$_{6-20}$ aryl, C$_{7-40}$ alkylaryl, C$_{7-40}$ arylalkyl, C$_{8-40}$ arylalkenyl, or taken together, two or more adjacent substituents form part of a ring structure having between 2 and 10 carbons;

Si is silicon;

N is nitrogen;

a=b=1, or a=0 when b=2;

and a catalyst activating compound.

2. The catalyst system of claim 1 wherein the transition metal catalyst component is represented by the formulae

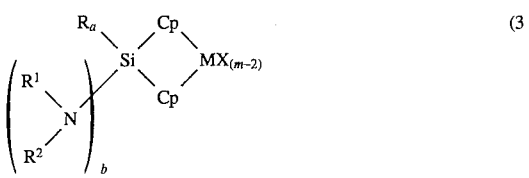

or

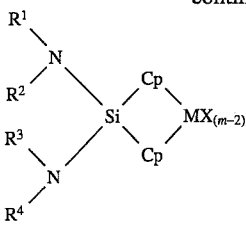 (4)

wherein L, Cp, M, X, m, R$_a$, R$^1$, R$^2$, R$^3$, R$^4$, Si, N, a, and b are as defined in claim 1.

3. The catalyst system of claim 1 wherein M is Group 4 transition metal.

4. The catalyst system of claim 1 wherein R, R$^2$, R$^3$, and R$^4$ are selected from the group consisting of C$_{1-20}$ alkyl, H, halogen, (CH$_3$)$_2$N,

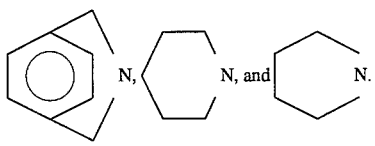

5. The catalyst system of claim 1 wherein the transition metal catalyst component is selected from the group consisting of (Me$_2$N)$_2$Si(t-BuCp)$_2$ZrCl$_2$,

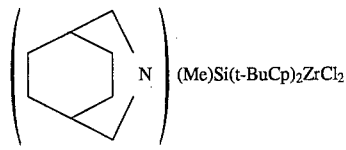

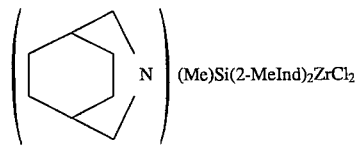

(Me$_2$N)$_2$Si-(2-MeInd)$_2$ZrCl$_2$,

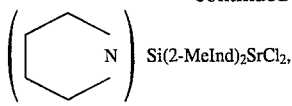

[(CH$_3$)$_2$N]$_2$Si(3-MeCp)$_2$ZrCl$_2$, and
(dicyclohexylamine)$_2$Si(2-MeInd)$_2$ZrCl$_2$ wherein Me=methyl, Ind=indenyl, and Bu=butyl.

6. The catalyst system of claim 1 wherein the catalyst activating compound is alumoxane.

7. The catalyst system of claim 1 wherein the catalyst activating compound is methylalumoxane.

8. The catalyst system of claim 1 wherein the catalyst activating compound is a single or mixed compound that will form a charge balanced catalytic species.

9. The catalyst system of claim 8 wherein the catalyst activating compound is a compound comprising a non coordinating anion.

10. The catalyst system of claim 9 wherein the non coordinating anion is tetra(pentafluorophenyl)boron.

11. The catalyst system of claim 8 wherein the catalyst activating compound is tris(pentafluorophenyl)borane.

12. The catalyst system of claim 1 placed on a support.

13. The catalyst system of claim 12 wherein the support is silica, alumina, or combinations thereof.

14. The catalyst system of claim 12 wherein the support is a magnesium compound.

15. The catalyst system of claim 12 prepolymerized with olefinic monomer having from about 2 to about 20 carbon atoms.

16. A process for polymerizing one or more monomers having between about 2 to about 20 carbon atoms comprising contacting the monomer(s) under suitable polymerization conditions with the catalyst system of claim 1.

17. The process of claim 16 wherein the monomers are alpha olefins, olefins, diolefins, cyclic olefins or acetylenically unsaturated monomer(s).

18. The process of claim 17 wherein an additive is employed during polymerization.

19. The process according to claim 16 wherein polymerization conditions are selected from bulk, gas, slurry, solution and high pressure phase polymerization.

* * * * *